United States Patent [19]

Binder et al.

[11] Patent Number: 5,086,180
[45] Date of Patent: Feb. 4, 1992

[54] SULPHAMOYLTHIOPHENES, A PROCESS THEIR PREPARATION

[75] Inventors: Dieter Binder, Vienna; Franz Rovenszky, Bruck an der Leitha; Norman Brunner, Hagenbrunn; Hubert P. Ferber, Ansfelden, all of Austria

[73] Assignee: Chemisch Pharmazeutische Forschungsgesellschaft m.b.H., Linz, Austria

[21] Appl. No.: 544,113

[22] Filed: Jun. 15, 1990

[30] Foreign Application Priority Data

Jul. 5, 1989 [AT] Austria .................. 1639/89

[51] Int. Cl.$^5$ ........................... C07D 239/74
[52] U.S. Cl. ............................... 546/172
[58] Field of Search ...................... 546/172

[56] References Cited

U.S. PATENT DOCUMENTS 4,675,405  6/1987  Musser et al. ............. 546/172
4,772,703  9/1988  Musser et al. ............. 544/283
4,778,803  10/1988  Binder et al. ............. 514/314

OTHER PUBLICATIONS

Morrison & Boyd, *Organic Chemistry*, 3rd Ed., pp. 583, 591, 848, (1976).

*Primary Examiner*—Alan L. Rotman
*Assistant Examiner*—Catherine S. Kilby Scalzo
*Attorney, Agent, or Firm*—Wenderoth, Lind & Ponack

[57] ABSTRACT

Sulphamoylathiophenes of the formula

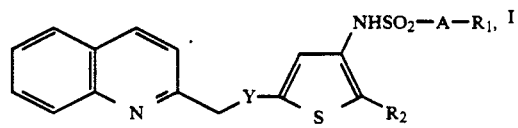

in which
Y denotes O or S,
A denotes a single bond or a straight-chain or branched alkylene group having 1-5 carbon atoms,
$R_1$ denotes methyl or trifluoromethyl and
$R_2$ denotes hydrogen or a group COOH or $COOR_3$, in which
$R_3$ represents $(C_1-C_4)$-alkyl, and, in the case in which $R_2$ denotes a group COOH, their pharmaceutically tolerable salts, a process for their preparation, pharmaceutical preparations which contain these compounds and their use in medicaments as leukotriene antagonists for the treatment of asthma and allergies.

2 Claims, No Drawings

SULPHAMOYLTHIOPHENES, A PROCESS THEIR PREPARATION

The invention relates to novel sulphamoylthiophenes, to a process for their preparation, to pharmaceutical preparations which contain these compounds and to their use in medicaments as leukotriene antagonists.

The invention relates to novel sulphamoylthiophenes of the formula

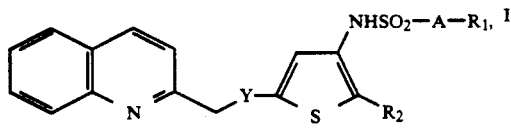

in which
Y denotes O or S,
A denotes a single bond or a straight-chain or branched alkylene group having 1-5 carbon atoms,
$R_1$ denotes methyl or trifluoromethyl and
$R_2$ denotes hydrogen or a group COOH or $COOR_3$, in which
$R_3$ represents $(C_1-C_4)$-alkyl,
and, in the case in which $R_2$ denotes a group COOH, to their pharmaceutically tolerable salts, to a process for their preparation, to pharmaceutical preparations which contain these compounds and to their use in medicaments as leukotriene antagonists.

A preferred class of compounds of the formula I contains those compounds in which A denotes a single bond and R denotes trifluoromethyl.

Particularly preferred individual compounds are: methyl 5-(2-quinolinylmethoxy)-3-(1,1,1-trifluoromethylsulphamoyl)-2-thiophenecarboxylate. 5-(2-quinolinylmethoxy)-3-(1,1,1-trifluoromethylsulphamoyl)-2-thiophenecarboxylic acid. 1,1,1-trifluoro-N-[5-(2-quinolinyl-methoxy)-3-thienyl]-methanesulphonamide.

The expression $(C_1-C_4)$-alkyl used in this description indicates straight-chain or branched saturated hydrocarbon radicals having 1 to 4 carbon atoms, such as, for example, methyl, ethyl, propyl, isopropyl, butyl, isobutyl and tert. butyl.

The compounds of the general formula I are prepared by a process in which
a) a compound of the formula

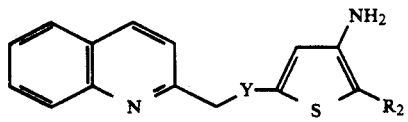

in which Y denotes O or S and $R_2$ denotes a group $COOR_3$, where $R_3$ represents $(C_1-C_4)$-alkyl, is reacted with a compound of the formula

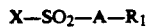

$$X-SO_2-A-R_1 \quad III$$

in which A and $R_1$ have the above meaning and X represents chlorine or a group $-O-SO_2-A-R_1$, where A and $R_1$ have the above meaning, in an inert organic solvent, b) if desired, an ester of the formula I, obtained in process step a), in which Y, A and $R_1$ have the above meaning and $R_2$ represents a radical $COOR_3$, where $R_3$ denotes $(C_1-C_4)$-alkyl, is hydrolysed to give a free acid of the general formula I in which $R_2$ denotes a group COOH, and, if desired, converted into a pharmaceutically tolerable salt using inorganic or organic bases and c) if desired, a free acid of the formula I, obtained in process step b), in which $R_2$ represents a group COOH and Y, A and $R_1$ have the above meaning, is decarboxylated to give a compound of the formula I in which $R_2$ denotes hydrogen.

The reaction according to process step a) is best carried out by dissolving or suspending a compound of the formula II in an inert organic solvent, such as a halogenated organic solvent, for example methylene chloride or chloroform or an ether, for example diethyl ether, adding at least two equivalents of an inorganic or organic base such as triethylamine, pyridine, N-methylmorpholine or trimethylsilanolate, preferably triethylamine or pyridine, and adding dropwise a solution of a compound of the general formula III in the same solvent at a temperature between $-80°$ and $30°$ C., preferably between $-20°$ and $20°$ C. The reaction time is then between 30 minutes and 4 hours, preferably between 30 and 90 minutes.

The esters of the formula I thus obtained can be hydrolysed in a customary manner with alcoholic aqueous alkali according to process step b) to give the free carboxylic acids of the formula I. For this purpose, the ester is dissolved in a mixture of a lower aliphatic alcohol and water and 2 to 6 equivalents of alkali are added, preferably 2 to 4 equivalents. The mixture is then stirred at a temperature between $30°$ and $100°$ C. The reaction time in this case is between 2 and 24 hours, the higher temperatures being associated with the shorter reaction times.

The compounds of the formula I obtained, in which $R_2$ denotes a group COOH, can be converted with inorganic or organic bases into their pharmaceutically utilizable salts. The salt formation can be carried out, for example, by dissolving the compounds of the formula I mentioned in a suitable solvent, for example water or a lower aliphatic alcohol, adding an equivalent amount of the desired base, providing for thorough mixing and removing the solvent by distillation in vacuo after salt formation is complete. If desired, the salts can be recrystallized after isolation.

Pharmaceutically utilizable salts are, for example, metal salts, in particular alkali metal or alkaline earth metal salts, such as sodium, potassium, magnesium or calcium salts. Other pharmaceutically utilizable salts are, for example, also easily crystallizing ammonium salts. The latter are derived from ammonia or organic amines, for example mono-, di- or tri-lower (alkyl, cycloalkyl or hydroxyalkyl)amines, lower alkylenediamines or (hydroxy lower alkyl or aryl lower alkyl) lower alkylammonium bases, for example methylamine, diethylamine, triethylamine, dicyclohexylamine, triethanolamine, ethylenediamine, tris(hydroxymethyl)aminomethane, benzyltrimethylammonium hydroxide and the like.

The free acids obtained by process step b) or their salts can be decarboxylated to give compounds of the formula I in which $R_2$ denotes hydrogen. For this purpose, the starting material is dissolved or suspended in a suitable solvent, such as in cyclic or aliphatic ethers or in pyridine, aqueous ammonia solution or in a lower aliphatic alcohol and heated for between 15 minutes and 8 hours, preferably between 10 and 60 min, at a temperature between 40° and 90° C., preferably between 60° and 80° C., with thorough mixing.

The compounds obtained are worked up by methods which are customary and familiar to any person skilled in the art such as, for example, extraction, precipitation or recrystallization.

The compounds of the formula II can be prepared according to the following equation and the special instructions in the examples.

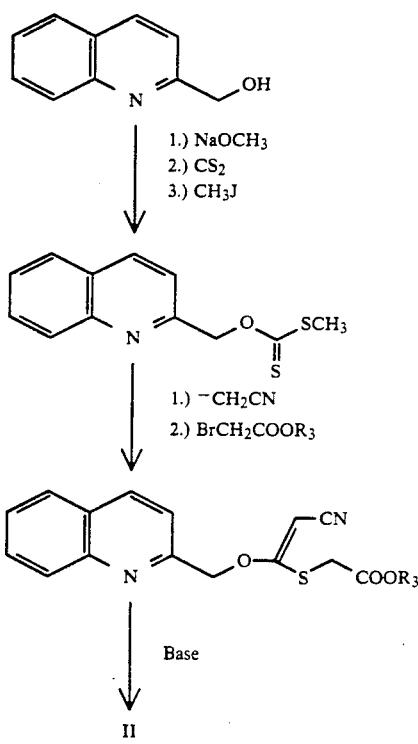

The sulphonyl chlorides or anhydrides of the formula III are known from the literature or commercially available.

The novel compounds of the formula I and, if $R_2$ denotes a group COOH, their pharmaceutically utilizable salts shown an excellent inhibitory action on leukotriences in in vivo and in vitro models. In addition, they inhibit the inflammatory processes in chronic disorders of the gastrointestinal tract, for example Crohn's disease, with lower side effects than known leukotriene antagonists.

On the basis of these pharmacological properties, the novel compounds can be used alone or in a mixture with other active substances in the form of customary pharmaceutical preparations for the treatment of diseases which are caused by an excess of leukotrienes, such as, for example, in asthma and allergies.

The compounds of the formula I are intended for use in humans and can be administered in a customary manner, such as, for example, orally, parenterally or by inhalation. They are preferably administered by inhalation, the daily dose being about 10 mcg to 10 mg/kg of body weight, preferably 50 to 500 mcg/kg of body weight. The treating physician may, however, depending on the general condition and the age of the patient, the appropriate substance of the formula I, the nature of the disease and the manner of the formulation, also prescribe doses above or below this.

If the substances according to the invention are used for prophylaxis, the dose varies in approximately the same bounds as in the treatment case. Administration by inhalation is also preferred in the case of prophylaxis.

The compounds of the formula I can be administered in medicaments alone or in combination with other pharmaceutically active substances, the content of the compounds of the formula I being between 0.1 and 99%. In general, the pharmaceutically active compounds are present in a mixture with suitable inert auxiliaries and/or excipients or diluents, such as, for example, pharmaceutically acceptable solvents, gelatin, gum arabic, lactose, starch, magnesium stearate, talc, vegetable oils, polyalkylene glycol, petroleum jelly and the like.

The pharmaceutical preparations may be present in solid form, for example as tablets, coated tablets, suppositories, capsules and the like, in liquid form, for example as solutions, suspensions or emulsions, in compositions with sustained release of the active compound, or in formulations for inhalation. If desired, they are sterilized and contain auxiliaries, such as preservatives, stabilizers or emulsifiers, salts for changing the osmotic pressure and the like. Formulations in spray containers contain propellants such as $CO_2$, nitrogen or halogenated hydrocarbons in addition to the abovementioned substances.

Pharmaceutical preparations may in particular contain the compounds according to the invention in combination with other therapeutically useful substances. Using these, the compounds according to the invention can be formulated, for example, together with the abovementioned auxiliaries and/or excipients of diluents to give combination preparations.

EXAMPLE 1

Methyl 5-(2-quinolinylmethoxy)-3-(1,1,1-trifluoromethylsulphamoyl)-2-thiophenecarboxylate 30.0 g (0.095 mol) of methyl 3-amino-5-(2-quinolinylmethoxy)thiophene-2-carboxylate are suspended in 400 ml of abs. methylene chloride at room temperature and 19.3 g (0.191 mol) of abs. triethylamine are added with stirring. The clear solution is cooled to 0° C. 47.1 g (0.167 mol) of trifluoromethanesulphonic anhydride dissolved in 50 ml of abs. methylene chloride are added dropwise at 0° C. in the course of 50 minutes. After completion of the addition, the reaction mixture is stirred at 0° C. for 30 minutes and then allowed to warm to room temperature. The brown reaction solution is diluted with 200 ml of methylene chloride and extracted by shaking twice with 100 of saturated sodium bicarbonate solution each time. The methylene chloride phase is extracted twice with 100 ml of 0.5N hydrochloric acid each time and then extracted by shaking with 50 ml of saturated sodium bicarbonate solution. The combined organic phases are dried over sodium sulphate/active carbon, filtered and evaporated. The crude product (40.5 g) is crystallized from 75 ml of ethanol.

Yield: 23.3 g of brown crystals (55% of theory, salt-free)

M.p.: 108°-110° C. (ethanol)

The starting material can be prepared as follows: O-(2-Quinolinylmethyl) S-methyl dithiocarbonate 80.0 g (0.503 mol) of 2-quinolinemethanol [V. Bockelheide and W. J. Linn; J. Am. Chem. Soc. 76, 1286

(1954)] are dissolved in 800 ml of absolute methanol and 94 ml of 5.4M (0.506 mol) sodium methoxide solution are added. The clear solution is evaporated and dried under high vacuum. 600 ml of acetone are added to the grey crystalline product (89.5 g), the suspension is cooled to 0° C. with stirring and 80.0 g (1.051 mol) of carbon disulphide are added in one portion. The mixture is stirred for a further 30 minutes at room temperature, a clear solution being formed. 85.8 g (0.602 mol) of methyl iodide are added to this solution in one portion. The mixture is stirred at 40° C. for 20 minutes, then 15.0 g of sodium sulphite are added to the reaction solution and it is evaporated. The residue is partitioned between 700 ml of saturated sodium sulphite solution and 500 ml of ether and the aqueous phase is extracted twice more using 300 ml of ether each time. The combined organic phases are washed once with 400 ml of water, dried over sodium sulphate/active carbon and evaporated. The crude product (118.6 g) is dissolved in 500 ml of diisopropyl ether at room temperature, active carbon is added, and the mixture is filtered and allowed to precipitate at −20° C. The product is filtered off with suction, digested twice with 50 ml of ice-cold diisopropyl ether each time and dried at 25° C./1 mbar for three hours.

Yield: 103.2 g of ochre-coloured crystals (82% of theory)

M.p.: 42°–43° C. (diisopropyl ether)

Methyl 3-amino-5-(2-quinolinylmethoxy)-2-thiophenecarboxylate 231 ml (0.578 mol) of 2.5M butyllithium solution in n-hexane is cooled to −80° C. with stirring and 300 ml of absolute tetrahydrofuran are added in the course of 25 minutes. 22.2 g (0.539 mol) of dry acetonitrile, dissolved in 100 ml of abs. tetrahydrofuran, are then added dropwise to the BuLi solution such that the temperature does not exceed −75° C. (30 minutes). The mixture is stirred further at −80° C. for 45 minutes. 133.6 g (0.536 mol) of O-(2-quinolinylmethyl) S-methyl dithiocarbonate, dissolved in 300 ml of absolute tetrahydrofuran, are then added dropwise to the reaction solution in the course of 35 minutes such that the temperature does not exceed −80° C. The reaction mixture is stirred further at −80° C. for one hour, then allowed to warm to 0° C. and evaporated. The remaining orange-red oil is dissolved in 300 ml of abs. tetrahydrofuran, cooled to −30° C. with stirring and 84.9 g (0.555 mol) of methyl bromoacetate, dissolved in 150 ml of absolute tetrahydrofuran, are added in one portion, the temperature rising to 5° C. The reaction mixture is subsequently heated under reflux for 150 minutes and then evaporated. The oily crude product is partitioned between 500 ml of saturated sodium carbonate solution and 800 ml of methylene chloride. The methylene chloride phase is extracted three times with 60 ml of 0.5N hydrochloric acid each time, dried over sodium sulphate/active carbon and cooled to 0° C. While stirring, the final product is precipitated as the hydrochloride using gaseous hydrogen chloride. The precipitate is filtered off with suction and washed twice with 100 ml of cold methylene chloride each time (75.4 g). The hydrochloride is suspended in 500 ml of ethyl acetate and extracted twice with 500 ml of ethyl acetate. The combined organic phases are dried over sodium sulphate/active carbon, filtered and evaporated. The residue (57.2 g) is recrystallized from 250 ml of ethanol, using active carbon.

Yield: 48.6 g of pale brown crystals (29% of theory)

M.p.: 143°–145° C. (diisopropyl ether)

EXAMPLE 2

5-(2-quinolinylmethoxy)-3-(1,1,1-trifluoromethylsulphamoyl)-2-thiophenecarboxylic acid 38.0 g (0.085 mol) of methyl 5-(2-quinolinylmethoxy)-3-(1,1,1-trifluoromethylsulphamoyl)-2-thiophenecarboxylate are dissolved in 350 ml of methanol and about 100 ml of 2N sodium hydroxide solution are added. The reaction mixture is heated under reflux and with stirring for 7 hours. The reaction solution is concentrated to 20% of its volume and diluted with 500 ml of water. The aqueous phase is extracted four times with a total of 500 ml of ether. The aqueous phase is cooled to 0° C. with stirring and acidified with 0.5N hydrochloric acid. The product precipitated in this way is filtered off with suction, digested twice with 50 ml of ice-cold ether each time and dried at 60° C./1 mbar.

Yield: 25.7 g of pale brown crystals (70% of theory)

M.p.: 101°–102° C. (dec.)

EXAMPLE 3

1,1,1-Trifluoro-N-[5-(2-quinolinylmethoxy)-3-thienyl]-methanesulphonamide 22.0 g (0.051 mol) of 5-(2-quinolinylmethoxy)-3-(1,1,1-trifluoromethylsulphamoyl)thiophene-2-carboxylic acid are suspended in 220 ml of water and 22 ml of conc. ammonia are added. Active carbon is added to the clear solution, and it is filtered, heated to 75° C. for 15 minutes with stirring and then allowed to cool to 35° C. The solution is acidified with 2N hydrochloric acid with vigorous stirring and immediately covered with 250 ml of ether. The aqueous phase is thoroughly stirred a further three times with 200 ml of ether each time, and the combined ether phases are dried over sodium sulphate/active carbon, filtered and evaporated. The crude product (15.8 g) is dissolved in 620 ml of diisopropyl ether at room temperature, active carbon is added, and the solution is filtered and allowed to crystallize at −20° C. in a deep-freeze. The product is filtered off with suction and digested twice with a little ice-cold diisopropyl ether. The final product is dried at 60° C./1 mbar.

Yield: 10.3 g of colourless crystals (52% of theory)

M.p.: 115.5°–116.5° C. (diisopropyl ether, dec.)

EXAMPLE 4

Guinea-pigs were anaesthetized with urethane (1.4 g/kg i.p.). A cannula was tied into the trachea and connected to a pneumotachograph (Messrs. Fleisch) which was connected to a Validyn differential pressure transducer (model DP 45-16) to measure the respiratory flow. The intrapleural pressure was measured continuously using a water-filled catheter which was tied into the intrapleural cavity and connected to a Validyn pressure transducer (model MPX-11 DP).

The data were recorded and evaluated in a Buxco Pulmonary Mechanics Analyzer (model 6) in order to obtain values for respiratory volume and resistance and compliance of the lungs.

In order to administer the substances, catheters were tied into the jugular vein and into the duodenum.

$LTD_4$ (leukotriene $D_4$, 0.6 mcg/kg i.v.) was administered 10 minutes after the intravenous administration or 20 minutes after the intraduodenal administration of the test substances As a control, animals were used which received the solvent without substances. All animals were pretreated with indomethacin (10 mg/kg i.v.) and propranolol (0.5 mg/kg i.v.) 20 and 15 minutes before administration of the test subtances. The test substances were dissolved in a mixture of DMSO and 0.15 mol/l of $NaHCO_3$ (1:1).

4 experiments were carried out per concentration value and the values were indicated as changes in the starting value in %. The results are presented in Table 1.

TABLE 1

|  | Resistance | Compliance |
|---|---|---|
| Control | +1,018% (±525) | −68% (±22) |
| 3 mg/kg i.v. | +74% (±31) | −23% (±7) |
| 5 mg/kg i.v. | +27% (±9) | −9% (±3) |
| 1 mg/kg i.d. | +450% (±132.3) | −43% (±17) |
| 3 mg/kg i.d. | +172% (±96) | −31% (±12) |
| 10 mg/kg i.d. | +20% (±8) | −18% (±9) | i.v.: intravenous
i.d.: intraduodenal

What we claim is:

1. A process for producing a compound of the formula

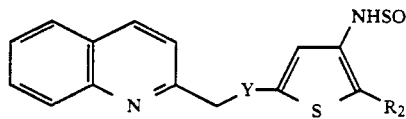

in which
Y denotes O or S,
A denotes a single bond or a straight-chain or branched alkylene group having 1–5 carbon atoms,
$R_1$ denotes methyl or trifluoromethyl and
$R_2$ denotes $COOR_3$, in which
$R_3$ denotes $(C_1\text{-}C_4)$-alkyl,
which comprises reacting a compound of the formula:

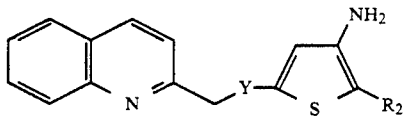

in which Y and $R_2$ have the above meaning with a compound of the formula $$X\text{—}SO_2\text{—}A\text{—}R_1 \qquad \text{III}$$

in which A and $R_1$ have the above meaning and X represents chlorine or a group $—O—SO_2—A—R_1$, where A and $R_1$ have the above meaning, in an inert organic solvent and in the presence of at least 2 equivalents of an inorganic or organic base.

2. A process for producing a compound of the formula

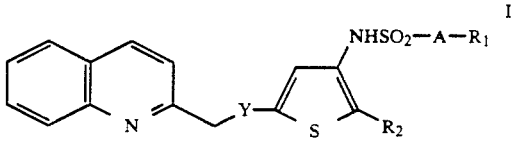

in which
Y denotes O or S
A denotes a single bond or a straight-chain or branched alkylene group having 1–5 carbon atoms,
$R_1$ denotes methyl or trifluoromethyl and
$R_2$ denotes hydrogen,
which comprises reacting a compound of the formula

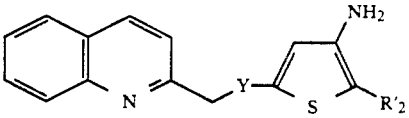

in which Y has the above meaning and $R'_2$ denotes $COOR_3$, in which $R_3$ represents $(C_1\text{-}C_4)$ alkyl with a compound of the formula $$X\text{—}SO_2\text{—}A\text{—}R_1 \qquad \text{III}$$

in which A and $R_1$ have the above meaning and X represents chlorine or a group $—O—SO_2—A—R_1$, where A and $R_1$ have the above meaning, in an inert organic solvent and in the presence of at least 2 equivalents of an inorganic or organic base, followed by hydrolyzing the ester to produce the corresponding carboylic acid and then decarboxylating the carboxylic acid.

* * * * *